US011759184B2

(12) United States Patent
Doyle et al.

(10) Patent No.: US 11,759,184 B2
(45) Date of Patent: Sep. 19, 2023

(54) APPARATUS, SYSTEM AND METHOD FOR DIAGNOSTIC IMAGING FORCEPS

(71) Applicant: Utah Valley University, Orem, UT (US)

(72) Inventors: Timothy E. Doyle, Orem, UT (US); Michael J. Salisbury, Orem, UT (US); Michael J. Bennett, Orem, UT (US)

(73) Assignee: Utah Valley University, Orem, UT (US)

( * ) Notice: Subject to any disclaimer, the term of this patent is extended or adjusted under 35 U.S.C. 154(b) by 301 days.

(21) Appl. No.: 16/057,720

(22) Filed: Aug. 7, 2018

(65) Prior Publication Data

US 2019/0038262 A1 Feb. 7, 2019

Related U.S. Application Data

(60) Provisional application No. 62/665,965, filed on May 2, 2018, provisional application No. 62/708,035, filed on (Continued)

(51) Int. Cl.
*A61B 8/08* (2006.01)
*A61B 8/00* (2006.01)
(Continued)

(52) U.S. Cl.
CPC ........ *A61B 10/0041* (2013.01); *A61B 6/4007* (2013.01); *A61B 6/502* (2013.01);
(Continued)

(58) Field of Classification Search
CPC ..... A61B 10/0041; A61B 17/29; A61B 17/30; A61B 2017/00079; A61B 2017/00106; A61B 2017/2825; A61B 2017/2926; A61B 2034/2051; A61B 2090/061; A61B 2090/065; A61B 2090/376; A61B 2090/3784; A61B 6/4007; A61B 6/502; A61B 6/56; A61B 8/0825; A61B 8/0858; A61B 8/4209; A61B 8/4494; A61B 8/56
See application file for complete search history.

(56) References Cited

U.S. PATENT DOCUMENTS

| 5,257,628 A * | 11/1993 | Ishiguro ................... A61B 8/12 600/440 |
| 2004/0059220 A1 * | 3/2004 | Mourad ................... A61B 8/08 600/442 |

(Continued)

OTHER PUBLICATIONS

PCT/US2018/045674, "Notification of Transmittal of the International Search Report and the Written Opinion of the International Searching Authority, or the Declaration", International Searching Authority, dated Oct. 1, 2018, pp. 1-9.

*Primary Examiner* — Yi-Shan Yang
*Assistant Examiner* — Alexei Bykhovski
(74) *Attorney, Agent, or Firm* — Kunzler Bean & Adamson (57) ABSTRACT

Provided herein are an apparatus, system, and method for a medical diagnostic and imaging forceps for determining the pathology of tissue in vivo during surgery, endoscopy, laparoscopy, or other medical procedure, the forceps comprising a platform for analyzing tissue pathology inside the body by way of sensors including without limitation conductivity, optical, tracking, and x-ray sensors.

24 Claims, 7 Drawing Sheets

Related U.S. Application Data on Nov. 30, 2017, provisional application No. 62/605,270, filed on Aug. 7, 2017.

(51) Int. Cl.

| | | |
|---|---|---|
| *A61B 6/00* | (2006.01) | |
| *A61B 17/29* | (2006.01) | |
| *A61B 10/00* | (2006.01) | |
| *A61B 17/30* | (2006.01) | |
| *A61B 17/00* | (2006.01) | |
| *A61B 17/28* | (2006.01) | |
| *A61B 90/00* | (2016.01) | |
| *A61B 34/20* | (2016.01) | |

(52) U.S. Cl.
CPC ............. *A61B 6/56* (2013.01); *A61B 8/0825* (2013.01); *A61B 8/0858* (2013.01); *A61B 8/4209* (2013.01); *A61B 17/29* (2013.01); *A61B 17/30* (2013.01); *A61B 8/4494* (2013.01); *A61B 8/56* (2013.01); *A61B 2017/00079* (2013.01); *A61B 2017/00106* (2013.01); *A61B 2017/2825* (2013.01); *A61B 2017/2926* (2013.01); *A61B 2034/2051* (2016.02); *A61B 2090/061* (2016.02); *A61B 2090/065* (2016.02); *A61B 2090/376* (2016.02); *A61B 2090/3784* (2016.02)

(56) References Cited

U.S. PATENT DOCUMENTS

| | | |
|---|---|---|
| 2004/0064151 A1 | 4/2004 | Mollenauer |
| 2006/0253107 A1 | 11/2006 | Hashimshony et al. |
| 2006/0287596 A1* | 12/2006 | Johnson ............ A61B 8/14 600/437 |
| 2008/0268374 A1* | 10/2008 | Tashiro ............ G03F 7/0045 430/280.1 |
| 2009/0054908 A1 | 2/2009 | Zand et al. |
| 2012/0071710 A1* | 3/2012 | Gazdzinski ............ A61B 1/273 600/101 |
| 2014/0358447 A1 | 12/2014 | Doyle et al. |

* cited by examiner

APPARATUS, SYSTEM AND METHOD FOR DIAGNOSTIC IMAGING FORCEPS

CROSS-REFERENCES TO RELATED APPLICATIONS

This Application claims priority to U.S. Provisional Patent Application No. 62/605,270 entitled INSTRUMENTED FORCEPS FOR PRECISION SURGERY and filed on Aug. 7, 2017 for Timothy E. Doyle, and claims priority to U.S. Provisional Patent Application No. 62/708,035 entitled GRAPHICAL USER INTERFACE AND SOFTWARE FOR THE IN VIVO USE OF ULTRASOUND INSTRUMENTED FORCEPS AND OTHER INSTRUMENTED SURGICAL TOOLS and filed on Nov. 30, 2017 for Timothy E. Doyle, and, claims priority to U.S. Provisional Patent Application No. 62/665,965 entitled APPARATUS, SYSTEM, AND METHOD FOR IMAGING FORCEPS FOR PRECISION SURGERY and filed on May 2, 2018 for Timothy E. Doyle, which is incorporated herein by reference.

FIELD OF THE INVENTION

This invention relates to surgical instrumentation and more particularly relates to forceps for precision surgery and diagnostics.

BACKGROUND

Description of the Related Art

The detection of cancer during or following surgery is critical for ensuring that all of the malignant tissue has been removed by the procedure and for determining whether the cancer has metastasized. This need is currently met post-surgically for most cancers, by performing conventional pathology analysis on the tissue edge of the primary resected tumor (surgical margins), on additional resected specimens that surrounded the primary tumor (cavity shavings or extended margins), and on the principal lymph nodes that drain the tumor region and are the first site for metastasis (sentinel lymph nodes). This process is time consuming, expensive, and often leads to great hardship for patients. For example, breast conservation surgery (BCS), also known as lumpectomy, is the surgery of choice for approximately 65% of breast cancer patients. However, BCS patients typically have to wait 4-5 days following surgery for the pathology analysis to be completed, and 20-40% of these patients end up requiring additional surgery to remove residual cancer that was missed by the first surgery.

Even surgeries that incorporate pathology analysis during the procedure, such as Mohs surgery for basal cell and melanoma skin cancers, can be a hardship on patients. For example, Mohs surgery requires successive removal of tissue layers, with pathology analysis being performed on each layer between excisions. Mohs surgery is therefore a very lengthy procedure that typically lasts for four hours or more while the patient is fully conscious and only under local anesthetic.

The majority of methods for detecting residual cancer in surgery function by examining tissue specimens ex vivo (outside the living body). However, the ability to examine tissues in vivo (inside the living body) for residual cancer would provide extensive benefits. The surgeon would be able to use the technology to perform more precise surgery by only extracting the tumor and other malignant tissue and leaving unaffected tissue in place. The technology would thus make cancer surgeries significantly more conservative. Benefits would include decreasing the re-excision rates for breast cancer surgery; reducing the procedure time for Mohs surgery; reducing the disfiguring effects of surgeries for breast, head, and neck cancers; preserving as much brain function as possible in brain tumor surgery; and being able to pinpoint isolated islands of cancer which have dispersed into surrounding tissue, which is a serious problem for certain types of brain cancer.

Thus, a need exists for a surgical instrumentation capable of sensing the surgery margins in real time and identifying remaining malignant tissue and other problems.

SUMMARY

From the foregoing discussion, it should be apparent that a need exists to detect and image cancerous tissue and tissue of other pathologies in real time during medical procedures such as surgery, in vivo, and at both the macroscopic (>1 mm) and microscopic (0.02-1.00 mm) scale. A need also exists for diagnostic technology that can be easily translatable to the operating room. Such a technology would ideally be based on a commonly used surgical instrument that can be used directly by the surgeon for immediate tissue assessment without the need for additional instruments within the surgical cavity, additional time to scan tissue with a secondary device, or additional personnel to operate a secondary device and interpret the results. It would also be advantageous if the technology were label-free, providing diagnostic capabilities without the need for tissue labeling with radiotracers, fluorescent biomarkers, or contrast agents. Finally, the ability of the invention to provide broad pathology diagnostic capabilities would be of significant benefit. For example, multi-category detection capabilities for pathology beyond that of binary differentiation (e.g., benign versus malignant tissue) would be important for identifying premalignant and atypical pathologies.

The present invention has been developed in response to the present state of the art, and in particular, in response to the problems and needs in the art that have not yet been fully solved by currently available surgical instrumentation. Accordingly, the present invention has been developed to provide an apparatus, system, and method for diagnostic and imaging forceps that overcome many or all of the above-discussed shortcomings in the art.

An apparatus is disclosed herein for determining the pathology of tissue in vivo during surgery, endoscopy, laparoscopy, or other medical procedure, the apparatus comprising a forceps comprising least one sensor on a tip of each arm of the forceps and wherein a sensor on one tip of the forceps transmits a pathology sensitive signal to a receiving sensor on the opposing tip of the forceps. In certain embodiments the apparatus comprises a sensor array on a tip of the forceps that transmits a pathology sensitive signal to a receiving sensor array on the opposing tip of the forceps. The apparatus sometimes comprises a spring and hinge mechanism at the back end of the forceps.

In some embodiments the apparatus comprises a sensor to measure the thickness of tissue during analysis and/or a three-dimensional motion tracking sensor or position sensor for determining the position of each pathology measurement during the medical procedure. Sensing modalities may comprise at least one of high-frequency ultrasound in the 10-100 MHz range, conductance and dielectric properties in the radiofrequency (RF) range, microwaves, terahertz waves, infrared light, visible light, ultraviolet light, and x-rays.

The arm of the forceps herein sometimes comprises a hollow chamber which may contain hardware elements for the sensor. In certain embodiments the apparatus herein comprises a sensor data transmitting module.

Further provided herein is a system to determine the pathology of tissue in vivo during surgery comprising a forceps comprising at least one sensor on a tip of each arm of the forceps. In various embodiments the system comprises a sensor on one tip of the forceps that transmits a pathology sensitive signal to a receiving sensor on the opposing tip of the forceps, a sensor data transmitting module, a sensor data receiving module, a sensor data interpretation module, and a sensor data interpretation display module.

In certain embodiments of the system herein the sensor detects at least one of high-frequency ultrasound in the 10-100 MHz range, conductance and dielectric properties in the radiofrequency (RF) range, microwaves, terahertz waves, infrared light, visible light, ultraviolet light, and x-rays. The sensor data interpretation module may perform calculations based on one or more of ultrasound transmission through tissue, light transmission through tissue, microelectrical currents through tissue, micro-electric fields through tissue, microwave transmission through tissue, terahertz wave transmission through tissue, tomographic reconstruction of pathology sensitive signals using sensor microarrays, charge-coupled device (CCD) array imaging of optical signals, micro-radiography using a weak radioactive point source and a miniature x-ray area image sensor.

In some embodiments of the system herein the sensor data interpretation module calculates a two-dimensional (2D) or three-dimensional (3D) pathology map of a surgical cavity, organ, or other body region where the medical procedure is performed. The sensor data interpretation module sometimes calculates a 2D or 3D microscale pathology map of the tissue region between the sensors at the forceps tips.

The sensor data interpretation display module of the system may comprise at least one of an audio, video, text, and visual display.

Also provided herein is a method for determining the pathology of tissue in vivo during surgery, endoscopy, laparoscopy, or other medical procedure, comprising the steps of providing a forceps comprising at least one sensor on a tip of each arm of the forceps wherein a sensor on one tip of the forceps transmits a pathology sensitive signal to a receiving sensor on the opposing tip of the forceps, applying the sensor to tissue during surgery or other procedure, transmitting sensed data to a data interpretation module, observing the interpretation of the data on a data display module, and adjusting the surgery or other procedure in light of the interpreted data.

According to the method herein the sensor sometimes detects at least one of high-frequency ultrasound in the 10-100 MHz range, conductance and dielectric properties in the radiofrequency (RF) range, microwaves, terahertz waves, infrared light, visible light, ultraviolet light, and x-rays.

In certain embodiments the sensor data interpretation module performs calculations based on one or more of ultrasound transmission through tissue, light transmission through tissue, micro-electrical currents through tissue, micro-electric fields through tissue, microwave transmission through tissue, terahertz wave transmission through tissue, tomographic reconstruction of pathology sensitive signals using sensor microarrays, charge-coupled device (CCD) array imaging of optical signals, micro-radiography using a weak radioactive point source and a miniature x-ray area image sensor. In various embodiments of the method herein the surgery comprises precision cancer surgery or Mohs surgery.

Reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussion of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize that the invention may be practiced without one or more of the specific features or advantages of a particular embodiment. In other instances, additional features and advantages may be recognized in certain embodiments that may not be present in all embodiments of the invention.

These features and advantages of the present invention will become more fully apparent from the following description and appended claims, or may be learned by the practice of the invention as set forth hereinafter.

BRIEF DESCRIPTION OF THE DRAWINGS

In order that the advantages of the invention will be readily understood, a more particular description of the invention briefly described above will be rendered by reference to specific embodiments that are illustrated in the appended drawings. Understanding that these drawings depict only typical embodiments of the invention and are not therefore to be considered to be limiting of its scope, the invention will be described and explained with additional specificity and detail through the use of the accompanying drawings, in which.

DETAILED DESCRIPTION

Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

Furthermore, the described features, structures, or characteristics of the invention may be combined in any suitable manner in one or more embodiments. In the following description, numerous specific details are supplied, to provide a thorough understanding of embodiments of the invention. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

Figure 1:
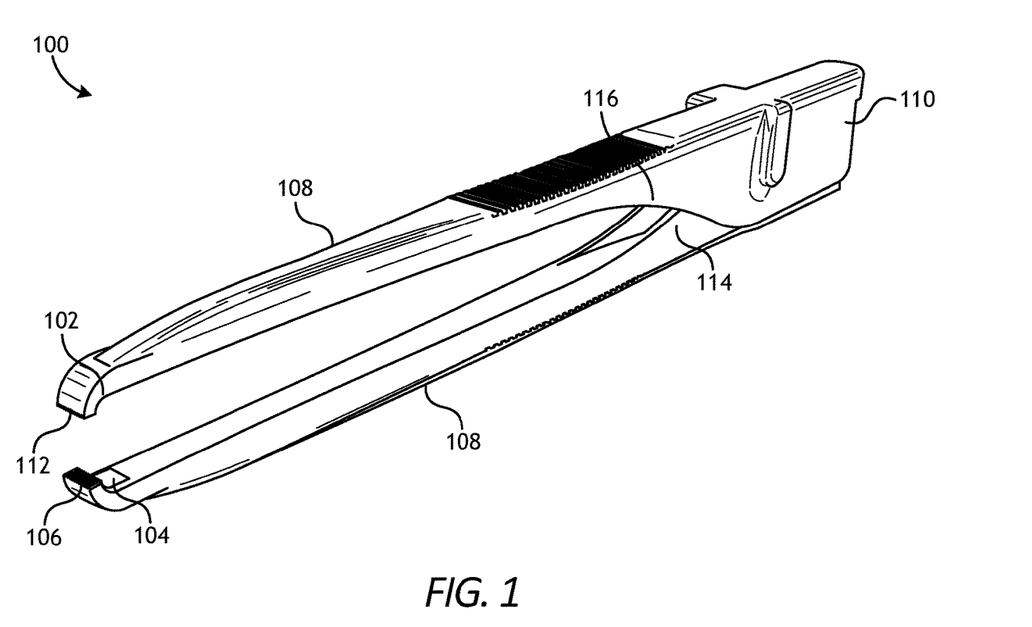
FIG. 1 is a line drawing depicting the primary components of the diagnostic imaging forceps.

FIG. 1 depicts an embodiment of a diagnostic imaging forceps 100 comprising a transmitting sensor 102 or sensor array 104 mounted on the tip 106 of a forceps arm 108, a receiving sensor 102 or sensor array 104 mounted on the tip 106 of the opposite arm 108 of the forceps 100 and directly opposing the transmitting sensor 102, a back end 110, ridges 112, a thickness sensor 114, and a three-dimensional (3D) motion tracking or position sensor 116. In some embodiments the back end 110 of the forceps 100 contains a pivot pin that attaches the two arms 108 of the forceps 100, a spring, and a thickness sensor. The forceps arms 108 may be hollow to enclose, shield, and protect components comprising wires and/or optical fibers connecting the sensors 102, 116 to instrumentation for actuating the transmitting sensor(s) 102, 116 and acquiring signals from the receiving sensor(s) 102,116. In certain embodiments the arms of the forceps 100 comprise ridges 112 for securely grasping tissue or other material.

In some embodiments the integration of high-frequency ultrasonic sensors 102 into the tips 108 of the forceps 100, results in a compact, miniaturized surgical tool for real-time diagnostic use by the surgeon during a medical procedure. In various embodiments the sensors 102 are pathology sensitive.

The forceps 100 function by grasping the tissue at the tips 108 and then collecting through-transmission measurements of the tissue. The design and configuration of the forceps 100 function as a platform for one or more of many types of sensors 102 to be used to probe tissue inside the surgical cavity, tissue opening, or body organ. The pathology sensitive sensors 102 may include ultrasonic sensors, dielectric sensors, conductivity sensors, optical sensors, microwave, terahertz wave, infrared, ultraviolet or x-ray sensors. The design and configuration of the forceps 100 functions as a platform for one or more of many types of sensors 102 to be used to probe tissue inside the surgical cavity or opening.

The spring and hinge mechanism at the back end 110 of the forceps may provide automatic closing action to the forceps 100. A thickness sensor 114 may measure tissue thickness during analysis, to aid in computation of parameters sensitive to pathology including without limitation ultrasonic attenuation, ultrasonic sound speed, dielectric constant, etc.

In certain embodiments 3D motion tracking sensors 116 robotically construct a global macroscopic map of the tissue pathology from a collection of forceps 100 measurements. The incorporation of sensor arrays 104 onto the tips 106 of the forceps 100 may enable the construction of 2D and/or 3D local microscopic maps of the tissue pathology from individual forceps 100 measurements.

The integration of microsensor technology into common surgical instruments such as forceps as provided herein may help guide surgeons during operations, provide instant diagnostic information, enable more precise and complete resection of malignancy or disease, and conserve as much unaffected tissue as possible. In addition to surgery, the forceps could be adapted for use during biopsy, endoscopic, and laparoscopic procedures, as well as for minimally invasive testing of skin, oral, rectal, and gynecological tissue.

Figure 2:
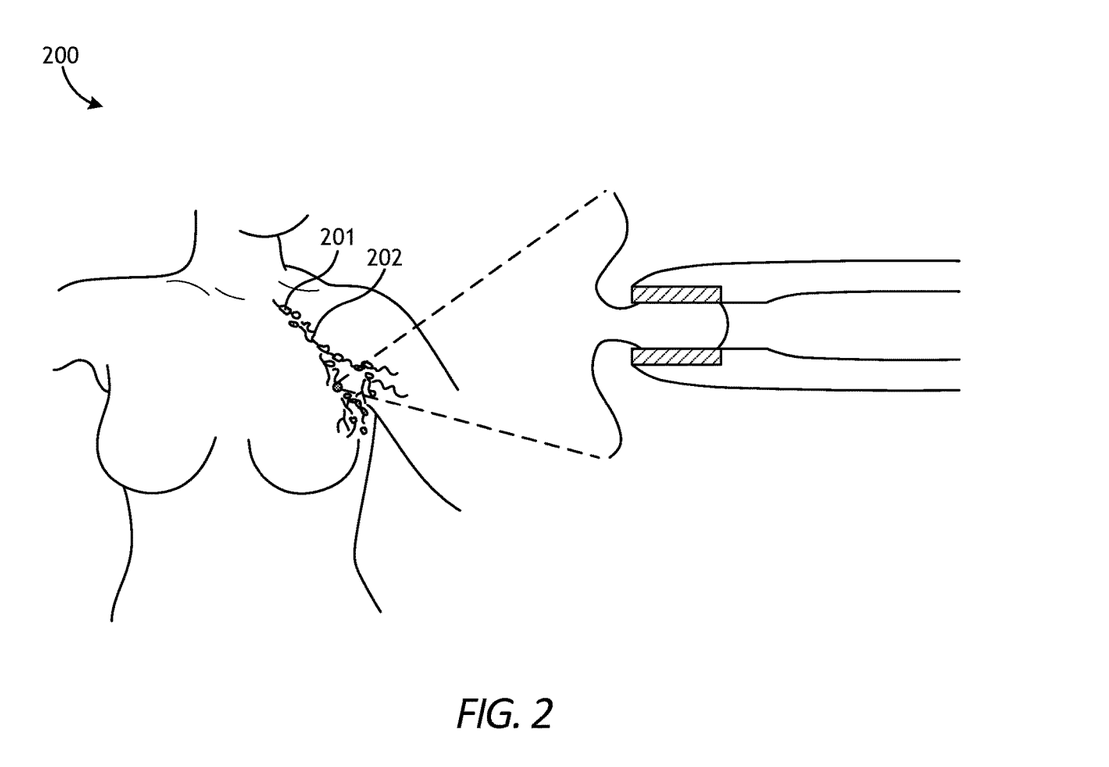
FIG. 2 is a line drawing illustrating one use of the diagnostic imaging forceps.

FIG. 2 depicts an embodiment of a use 200 of diagnostic imaging forceps 100 comprising determining the malignancy of lymph nodes 201 that are associated with a breast tumor by common lymphatic vessels 202. Such a procedure is usually performed as part of breast conservation surgery, also known as lumpectomy. The transmitting and receiving sensors 102, mounted on the tips 108 of the forceps 100 grasp each lymph node 201. The lymph node 201 is tested by transmitting energy through the tissue, including ultrasonic waves, radiofrequency electromagnetic radiation, microwaves, infrared radiation, optical radiation, x-rays, or other form of radiative energy. The pathology of the tissue is determined by scattering, absorption, dispersion, or other tissue property that alters the transmission of the energy and is sensitive to pathology.

The procedure provided herein may significantly reduce the number of additional surgeries that many patients, e.g., 20-40% of BCS patients, are required to endure to remove malignant tissue that was missed during the initial procedure.

It may result in the conservation of more unaffected tissue, ensuring that only malignant tissue was removed. For example, BCS patients often have several lymph nodes removed to ensure that the cancer has not metastasized. However, removal of multiple lymph nodes can lead to debilitating side effects, such as edema, infection, or limited use of the arm next to the affected breast. By determining the malignancy of lymph nodes in vivo during surgery, diagnostic imaging forceps may allow surgeons to preserve benign lymph nodes in the patient while ensuring malignant lymph nodes are resected.

Use of the disclosed technology may greatly increase the speed of certain oncological surgeries such as Mohs surgery. Mohs surgery is a specialized surgery performed on basal cell and melanoma skin cancer where slices of skin tissue are removed sequentially and deeper into the tissue after the tumor is excised. Each consecutive slice is examined by standard pathology between excisions. The surgery typically lasts four hours or longer due to the slow process of pathology, but technology for determining tissue malignancy rapidly, accurately, and with high sensitivity might greatly shorten the procedure time.

Figure 3:
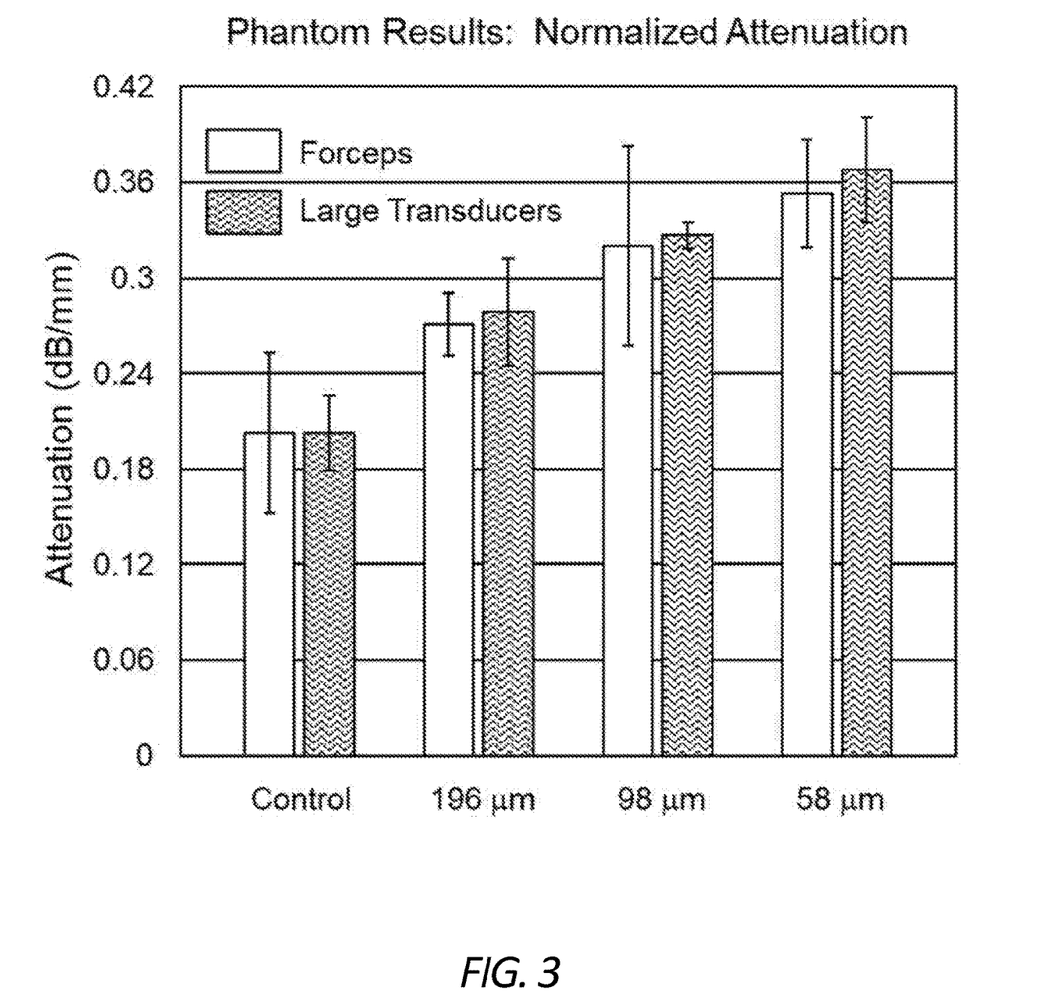
FIG. 3 is a bar chart comparing results from diagnostic imaging forceps with high-frequency polyvinylidene difluoride (PVDF) ultrasonic sensors (~20 MHz, 4×6 mm active element size) with those from standard piezoceramic ultrasonic transducers (50 MHz, 6.35-mm diameter active element size)

FIG. 3 is a bar chart comparing results from diagnostic imaging forceps 100 with high-frequency polyvinylidene difluoride (PVDF) ultrasonic sensors (~20 MHz, 4×6 mm active element size) with those from standard piezoceramic ultrasonic transducers (50 MHz, 6.35-mm diameter active element size). The test samples were agarose tissue phantoms with embedded polyethylene microspheres to vary ultrasonic attenuation, an ultrasonic parameter sensitive to tissue pathology. The chart demonstrates that the forceps provide ultrasonic attenuation measurements with trends and uncertainties comparable to those from standard ultrasonic instrumentation.

Figure 4:
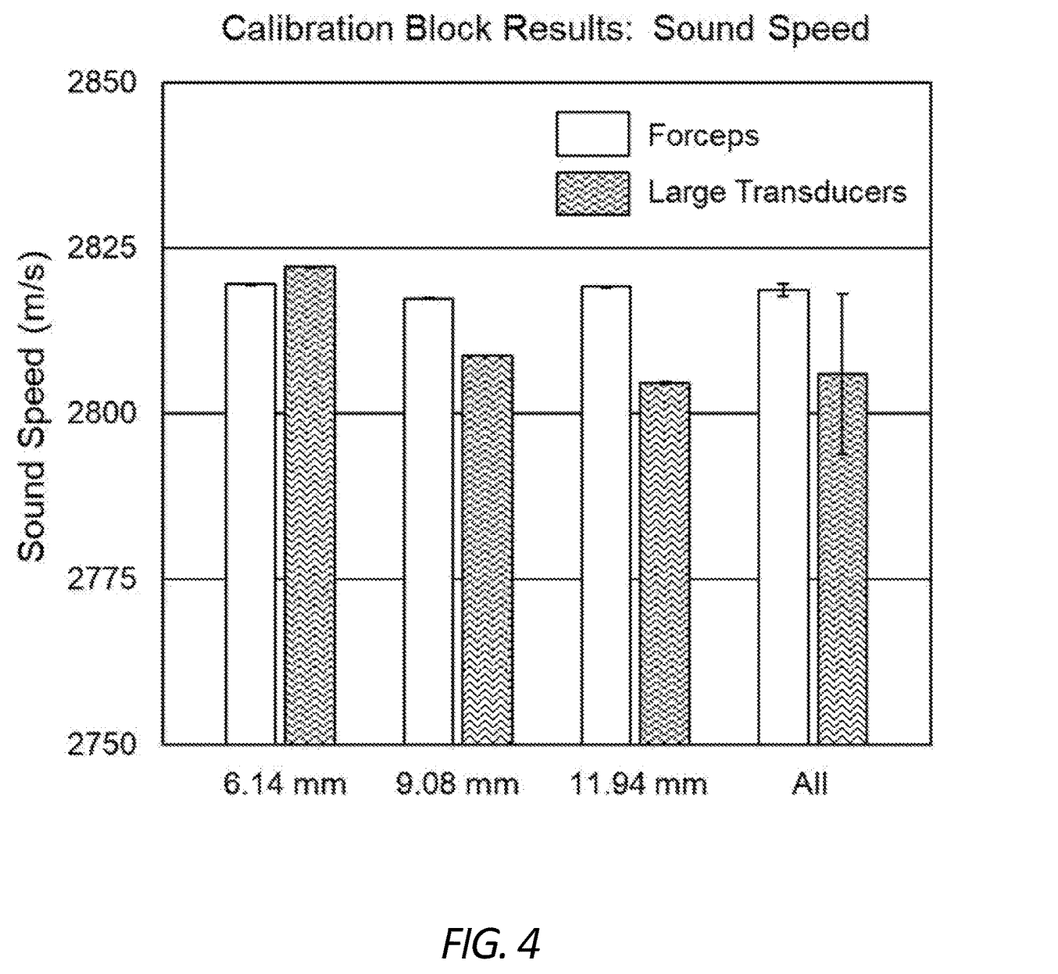
FIG. 4 is a bar chart comparing results from diagnostic imaging forceps with high-frequency polyvinylidene difluoride (PVDF) ultrasonic sensors (~20 MHz, 4×6 mm active element size) with those from standard piezoceramic ultrasonic transducers (50 MHz, 6.35-mm diameter active element size)

FIG. 4 is a bar chart comparing results from diagnostic imaging forceps 100 with high-frequency polyvinylidene difluoride (PVDF) ultrasonic sensors (~20 MHz, 4×6 mm active element size) with those from standard piezoceramic ultrasonic transducers (50 MHz, 6.35-mm diameter active element size). The test sample was an acrylic calibration block with steps of varying thickness. The calibration block was used to collect accurate measurements of ultrasonic sound speed, an ultrasonic parameter sensitive to tissue pathology. The chart demonstrates that the forceps provide ultrasonic sound speed measurements with greater consistency and reproducibility than those from standard ultrasonic instrumentation.

Figure 5:
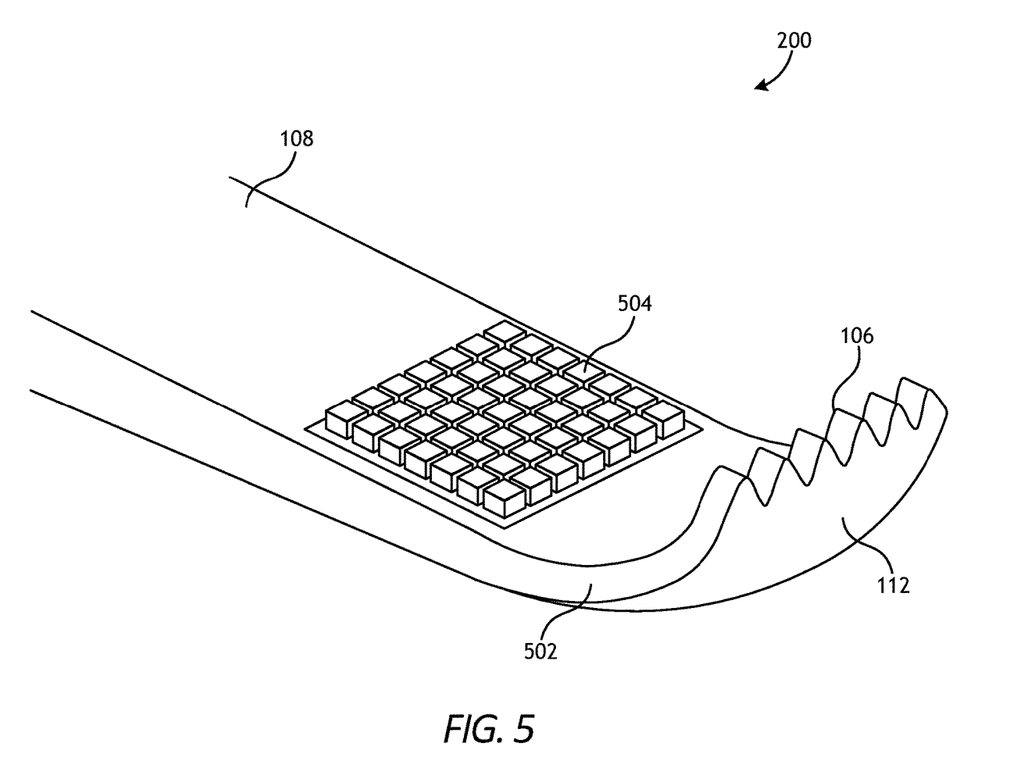
FIG. 5 is a line drawing depicting an embodiment of a tip of a diagnostic imaging forceps, illustrating an array of sensor elements mounted on the tip.

FIG. 5 depicts an embodiment of a tip 106 of a diagnostic imaging forceps 100, comprising an array 504 of sensor 102 elements mounted on the tip 106. The opposing tip 106 may have a similar design, with one tip 106 having a transmitting array 104, and the other tip having a receiving array 104. The forceps 100 tip 108 design in this drawing is based on Martin forceps, a standard surgical forceps with curved grasping features 502 at the ends of the tips 106. The 49-element array 504 is for illustrative purposes only. The array and element size may depend on current technology and state of the art for the type of sensor (ultrasonic, microwave, infrared, optical, x-ray, etc.).

In various embodiments rugged yet sensitive polyvinylidene difluoride (PVDF) elements such as miniature ultrasonic sensors 102 mounted on the forceps 100 provide for repeated and reproducible use. The incorporation of 3D motion tracking sensors 116 into the forceps 100 may robotically construct a global macroscopic map of the tissue pathology from a collection of forceps measurements. In some embodiments the incorporation of sensor arrays 104 onto the tips 106 of the forceps 100 aids in the construction of 2D and/or 3D local microscopic maps of the tissue pathology from individual forceps measurements.

Three-dimensional (3D) macroscopic imaging of tissue pathology inside the surgical cavity or other body opening is achieved using 3D motion tracking sensors 116 integrated into the forceps 100 to automatically locate the forceps tips 106 during sensor data acquisition. The pathology result from each acquisition point is then used in real time to build a global 3D map of the tissue pathology inside the surgical, body, organ, or tissue cavity during the procedure. The use of sensor arrays 104 attached at the tips 106 of the forceps 100 also provides two-dimensional (2D) and 3D imaging capability of the local microscopic pathology of the probed tissue. Methods for microscopic imaging include, but are not limited to, tomographic reconstruction of ultrasonic signals using ultrasonic microarrays 504, charge-coupled device (CCD) array 104 imaging of optical signals, and microradiography using a weak radioactive point source 102 and a miniature x-ray area image sensor 104.

To image the macroscopic pathology of the surgical cavity, the exposed tissue in the surgical cavity is sampled at multiple locations by the pathology sensitive sensors 102 of the forceps 100. During the sampling, 3D motion-tracking sensors 116 incorporated into the forceps 100 are used to pinpoint the position of the forceps tips 106 at each sampled location. The position information is then combined with the determined tissue pathology at the sampled location to construct a pathology map of the surgical cavity.

One embodiment of the invention uses sensors 102 or sensor arrays 104 comprised of piezoelectric elements to acquire through-transmission measurements of high-frequency ultrasound in the 10-100 MHz frequency range. The piezoelectric elements may consist of a piezoceramic material, piezoelectric single crystals, or a piezoelectric polymer such as polyvinylidene difluoride (PVDF). In certain embodiments the sensors 102 or sensor arrays 104 are mounted at the tips 106 of the forceps 100, and the arms 108 of the forceps 100 are hollow to house the electrical wires to the elements. The thickness sensor 114 housed on the back end 110 of the forceps 100 measures the thickness of the tissue during testing. The high-frequency ultrasound provides measurements on ultrasonic sound speed, attenuation, and spectral characteristics that may be used to image the global 3D macroscopic distribution of the tissue pathology (using 3D motion tracking sensors) and/or the local 3D microstructure of the tissue pathology using sensor arrays.

One embodiment of the invention uses optical sensors 102—comprised of a semiconductor laser array (either monochromatic or polychromatic) as the transmitting component, and a charge-coupled device (CCD) imaging array (again, either monochromatic or polychromatic) as the receiving component—to acquire through-transmission measurements of Raman, extinction, fluorescence, and other types of optical spectra. As with the ultrasound forceps 100 above, the forceps 100 are configured with electrical wires housed in the forceps arms. Individual laser elements from the semiconductor laser array transmit light from the tip 106 of one arm 108 to the tip 106 of the opposing arm 108, thereby transmitting light through the tissue. The sensor elements 102 of the CCD imaging array in the opposing tip 106 receive the transmitted light after passing through the tissue. The received measurements are spectroscopically analyzed and reconstructed using computed tomography into a 3D rendition of the tissue pathology.

In certain embodiments the sensors 102 comprise a weak, x-ray emitting, radioisotope source attached to one tip 106 of the forceps 100, and a miniature, solid-state, x-ray detector array attached to the opposite tip 106 to image the x-ray density of the grasped tissue. Limited elemental analysis of the tissue may also be possible using an energy dispersive x-ray detector, thereby producing an elemental composition image of the tissue.

The forceps 100 sometimes uses sensor arrays 104 comprising electrically conductive elements. Minute electrical currents from each element on the transmitting array 104 are propagated through the tissue to similar electrically conductive elements on the receiving array 104. From the voltage drops of each measurement, a 3D image of the tissue resistivity can be reconstructed from computed tomography analysis.

More than one type of sensor 102 or array 104 may be added to the forceps 100 to increase the diagnostic capability of the micro-imaging surgical device, such as ultrasonic with conductive sensors, x-ray with optical sensors, and others. A specific application of the invention is precision cancer surgery to ensure the complete removal of malignant tissue from the resection cavity during surgery, including residual cancer in margins, invasive cancer beyond the primary tumor, and metastatic cancer in lymph nodes. The invention may also be used for rapid assessment of surgical specimens ex vivo for residual cancer, for example, during Mohs surgery.

Figure 6:
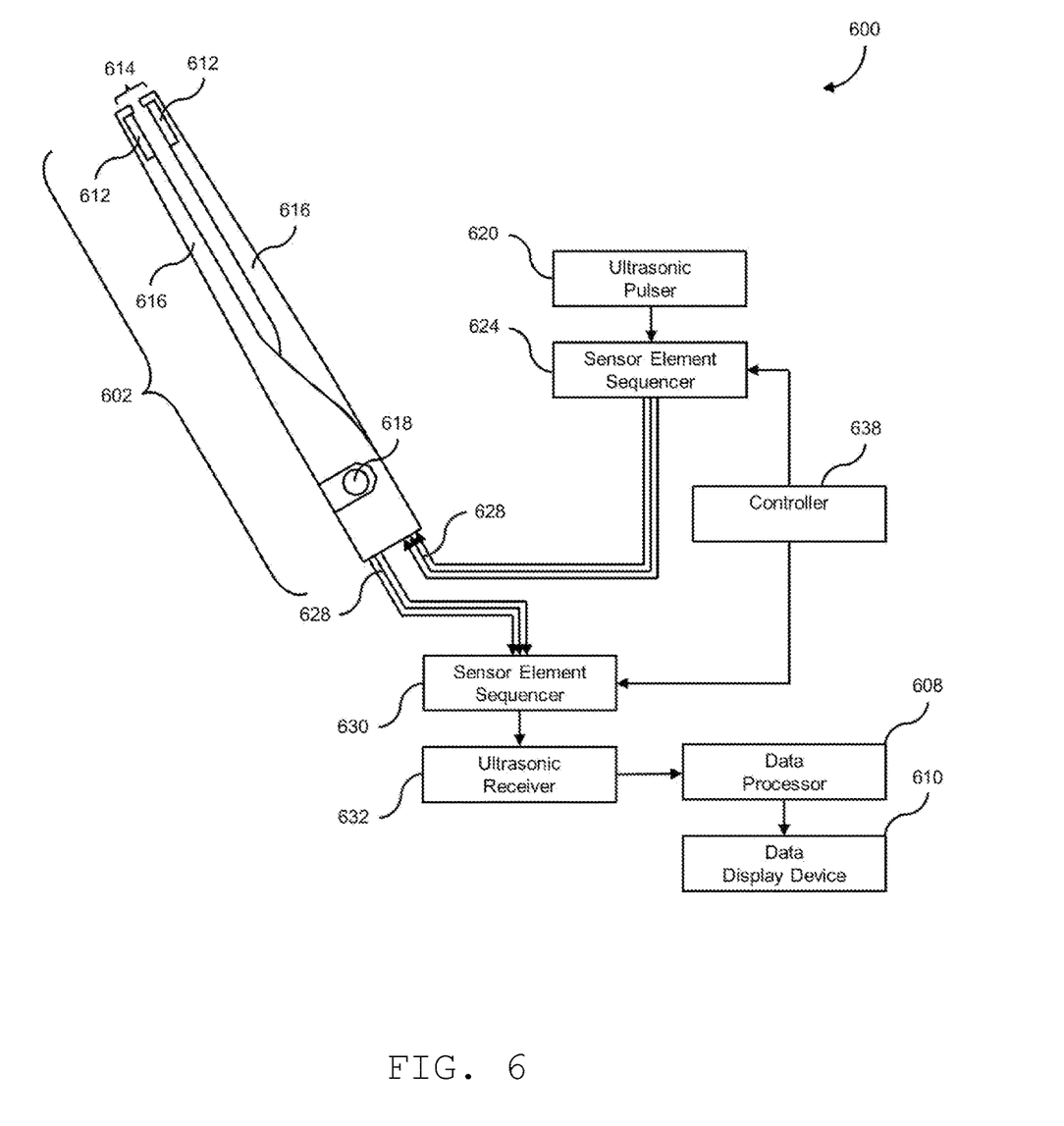
FIG. 6 is a schematic line drawing depicting a system for a diagnostic imaging forceps.

FIG. 6 depicts an embodiment of a system 600 according to the present invention, the system comprising a forceps 602 a sensor element sequencer 624, an ultrasonic pulser 620 for transmitting data, a sensor element sequencer 630, an ultrasonic receiver 632 for receiving data, a data processor 608, a data display device 610, a sensor array 612, a tip of the forceps arm 614, an arm of the forceps 616, paired tissue thickness, tracking, and/or position sensors 618, a multichannel cable 628, and a controller 638 for selecting sensor array elements for transmitting and receiving.

In certain embodiments the forceps 602 comprises a sensor array 612 on a tip 614 of at least one arm 616 of the forceps 602. The sensor array 612 on one tip 614 of the forceps 602 transmits a pathology sensitive signal to a receiving sensor 612 on the opposing tip 614 of the forceps 602. The forceps 602 may further comprise a tracking/position sensor 618.

In various embodiments the ultrasonic pulser 620 and sensor element sequencer 624 transmit high-voltage pulses to the transmitting sensor array 612 which generates and broadcasts ultrasound through the tissue region. The receiving sensor and or sensor array 612 receives and converts the ultrasound to electrical data signals which are transmitted to the element sequencer 630 and ultrasonic receiver 632, which makes the data accessible to the data processor 608 which performs the relevant calculations. The data display device 610 accesses the calculations and displays the result.

The sensor array 612 may detect at least one of high-frequency ultrasound in the 10-100 MHz range, conductance and dielectric properties in the radiofrequency (RF) range, microwaves, terahertz waves, infrared light, visible light, ultraviolet light, and x-rays.

In some embodiments the data processor 608 performs calculations based on at least one of ultrasound transmission through tissue, light transmission through tissue, micro-electrical currents through tissue, micro-electric fields through tissue, microwave transmission through tissue, terahertz wave transmission through tissue, tomographic reconstruction of pathology sensitive signals using sensor microarrays, charge-coupled device (CCD) array imaging of optical signals, micro-radiography using a weak radioactive point source and a miniature x-ray area image sensor.

The data processor 608 sometimes calculates a two-dimensional (2D) or three-dimensional (3D) pathology map of a surgical cavity, organ, or other body region where the medical procedure is performed and/or the data processor 608 may calculate a 2D or 3D microscale pathology map of the tissue region between the sensors at the forceps tips.

In various embodiments the data display device 610 comprises at least one of an audio, video, text, and a visual display. The data processor 608 may query the forceps 602 for additional data. This may be done directly or via a reverse flow through the sensor element sequencer 630 and ultrasonic receiver 632 and the sensor element sequencer 624 and ultrasonic pulser 620. In certain embodiments the ultrasonic pulser 620 produces a time-dependent voltage variation to activate one or more sensor elements in the transmitting sensor array 612. The voltage variation may include a spike pulse, a half-wave pulse, a square-wave pulse, a tone burst, or other arbitrary waveform. The sensor elements sequencers 624 sometimes selects which sensor element or configuration of sensor elements of the transmitting sensor array 612 to activate. The sensor element sequencer 630 sometimes select which sensor element or configuration of sensor elements of the receiving sensor array 612 to activate. This switching operation varies which sensor element or configuration of sensor elements are activated during a sequence of measurements to collect data for reconstructing a 2D or 3D pathology image of the interrogated tissue region. The multichannel cable 628 may carry the voltage variations from the ultrasonic pulser 620 and sensor element sequencer 624 to one or more sensor elements in the transmitting sensor array 612, or may carry the voltage signals from one or more sensor elements in the receiving sensor array 612 to the sensor element sequencer 630 and ultrasonic receiver 632. In various embodiments the sensor elements sequencers 624, 630 select which sensor element or configuration of sensor elements of the transmitting sensor array 612 to pulse and receiving sensor array 612 to read. This switching operation varies which sensor element or configuration of sensor elements are pulsed and read during a sequence of measurements to collect data for reconstructing a 2D or 3D pathology image of the interrogated tissue region. The data processor 608 may computationally process the read voltage signals to correlate the signal properties (for example, voltage decrease, signal transmission time through tissue, and/or spectral properties) to pathology-sensitive tissue properties (for example, tissue stiffness, tissue viscoelasticity, size of cell nuclei, distribution of mitochondria in cells, and/or chemical composition of tissue). In some embodiments the data processor 608 uses a plurality of pathology-sensitive property measurements from a specified sequence of different sensor elements, different configurations of sensor elements, and/or different forceps positions to computationally build a 2D or 3D image or map of the pathology of the interrogated tissue region. In certain embodiments the data processor 608 selects sensor array elements for transmitting and receiving and instructs the sensor element sequencer 624 and the ultrasonic pulser 620 on the selection of sensor element, configuration of sensor elements, and activation sequence thereof. In certain embodiments the controller module for selecting sensor array elements for transmitting and receiving instructs the sensor element sequencer 624 and ultrasonic pulser 620 on the timing or phase delay to be applied to the voltage variations between sensor elements in a configuration of sensor elements. In certain embodiments the controller module for selecting sensor array elements for transmitting and receiving instructs the sensor element sequencer 630 on the selection of sensor element, configuration of sensor elements, and read sequence thereof.

Figure 7:
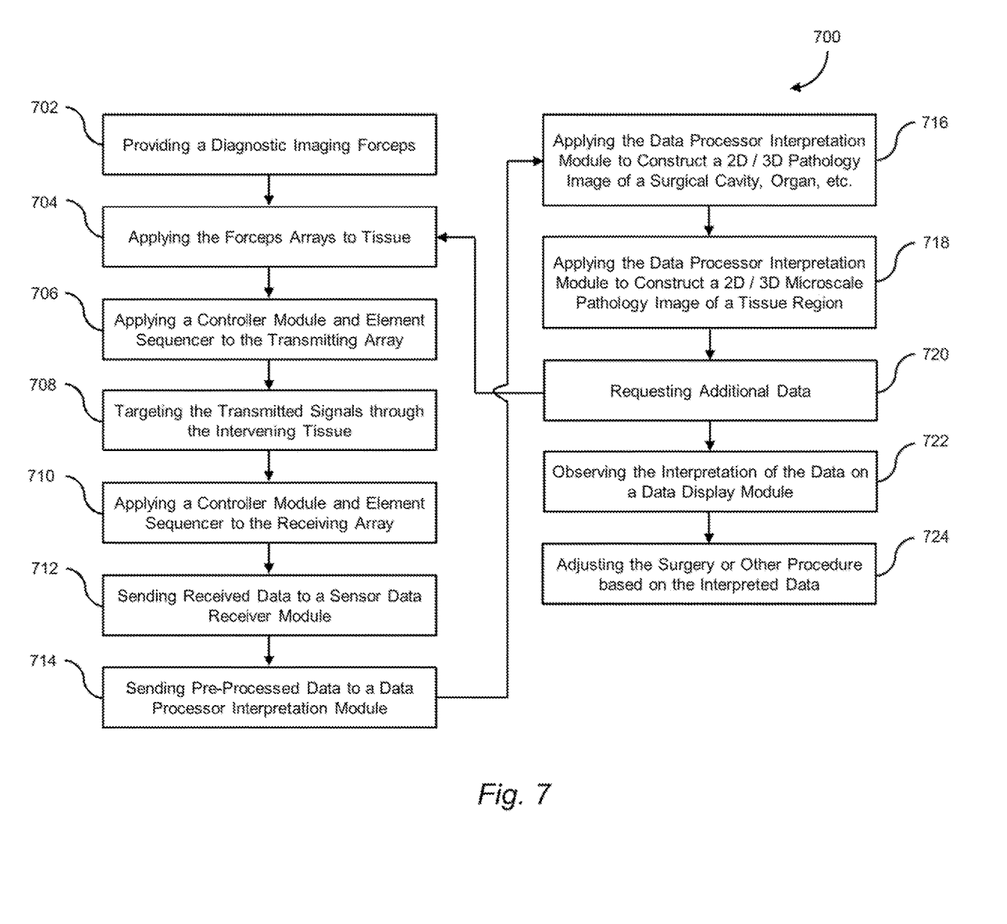
FIG. 7 is a schematic flow chart depicting a method for a diagnostic imaging forceps.

FIG. 7 depicts an embodiment of a method 700 for a diagnostic imaging forceps, the method 700 comprising the steps of: providing 702 a diagnostic imaging forceps 602 comprising at least one sensor 612 on a tip 614 of each arm 616 of the forceps 602, applying 704 the sensor 612 of the forceps 602 to an intervening tissue during surgery or other procedure; applying 706 a controller module and sensor element sequencer to modulate a transmitted signal of each sensor element or group of sensor elements in the transmitting sensor array to scan the intervening tissue; targeting 708 the transmitted signals through the intervening tissue; applying 710 a controller module and sensor element sequencer to each sensor element or group of sensor elements in the receiving sensor array to coordinate with a scan transmission of the transmitting sensor array; sending 712 received data to a sensor data receiver module to pre-process data with at least one of an amplifier, filter, and rectifier; sending 714 pre-processed data to a data processor interpretation module; applying 716 the data processor interpretation module to construct a 2D or 3D image of a pathology of a surgical cavity, organ, or other body region where a medical or other procedure is performed; applying 718 a data processor interpretation module to construct a 2D or 3D microscale image of the pathology of a tissue region between the sensor arrays at the forceps tips; requesting 720 additional data 7; observing 72 the interpretation of the data on a data display module 610 and adjusting 724 the surgery or other procedure based on the interpreted data.

In some embodiments of the method 700 the sensor 612 detects at least one of high-frequency ultrasound in the 10-100 MHz range, conductance and dielectric properties in the radiofrequency (RF) range, microwaves, terahertz waves, infrared light, visible light, ultraviolet light, and x-rays.

According to the method 700 the sensor data interpretation module 608 may perform calculations based on at least one of ultrasound transmission through tissue, light transmission through tissue, micro-electrical currents through tissue, micro-electric fields through tissue, microwave transmission through tissue, terahertz wave transmission through tissue, tomographic reconstruction of pathology sensitive signals using sensor microarrays, charge-coupled device (CCD) array imaging of optical signals, micro-radiography using a weak radioactive point source and a miniature x-ray area image sensor.

In various embodiments of the 700 method the surgery comprises precision cancer surgery and/or Mohs surgery.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An apparatus for determining microcellular characteristics of a tissue the apparatus comprising:
   a forceps comprising a first arm and an opposing second arm;
   the first arm of the forceps comprising at least one transmitting sensor array on a tip of the first arm of the forceps wherein the transmitting sensor array comprises two or more homogenous or mixed sensor elements or groups of sensor elements and is configured to transmit a microcellular characteristic-sensitive signal through the tissue;
   the second arm of the forceps comprising at least one receiving sensor array on a tip of the opposing second arm of the forceps wherein the receiving sensor array comprises a second two or more homogenous or mixed sensor elements or groups of sensor elements and is configured to receive the microcellular characteristic-sensitive signal transmitted through the tissue from the opposing transmitting sensor array;
   a first sensor element sequencer and ultrasonic pulser on or connected to the first arm of the forceps;
   a second sensor element sequencer and ultrasonic receiver on or connected to the second arm of the forceps;
   a first controller on or connected to the first arm of the forceps, wherein each of the first sensor element sequencer, ultrasonic pulser, and first controller is configured to generate a scan transmission of the transmitting sensor array;
   a second controller on or connected to the second arm of the forceps wherein each of the second sensor element sequencer and second controller is configured to coordinate with the scan transmission of the transmitting sensor array; and
   a three-dimensional motion tracking sensor or position sensor for determining the position of each characteristic measurement during use.

2. The apparatus of claim 1, further comprising a spring and hinge mechanism at the back end of the forceps.

3. The apparatus of claim 1, further comprising a geometric sensor to measure tissue thickness during tissue analysis.

4. The apparatus of claim 1, further comprising individual or mixed sensor elements in the opposing sensor arrays at the tips of the opposing arms of the forceps, the sensor elements having a sensing modality comprising at least one of high-frequency ultrasound in the 10-100 MHz range, conductance and dielectric properties in the radiofrequency (RF) range, microwaves, terahertz waves, infrared light, visible light, ultraviolet light, and x-rays.

5. The apparatus of claim 4 further comprising a sensor data transmitting module.

6. The apparatus of claim 1, wherein the opposing arms of the forceps comprise at least one hollow chamber and wherein the hollow chamber contains hardware elements for the opposing sensor arrays.

7. The apparatus of claim 1 wherein the transmitting sensor array on the tip of the first arm of the forceps transmits a tissue/cellular characteristic sensitive signal and the receiving array on the second arm of the forceps receives reflections of the signal from within the tissue.

8. The apparatus of claim 1 further comprising an optical sensor comprised of a monochromatic or polychromatic semiconductor laser array and a monochromatic or polychromatic charge-coupled (CCD) imaging array for through-transmission measurements of at least one of Raman, extinction, fluorescence, and other optical spectra.

9. A system to determine microcellular characteristics of a tissue, the system comprising:
   a forceps comprising a first arm comprising at least one transmitting sensor array or group of arrays on a tip of the first arm, and comprising a second opposing arm comprising at least one receiving sensor array or group of arrays on a tip of the opposing second arm wherein the transmitting sensor array on the tip of the first arm of the forceps is configured to transmit a microcellular characteristic-sensitive signal through a tissue to the receiving sensor array on the tip of the opposing second arm of the forceps, and wherein each sensor array or group of sensor arrays comprises two or more homogeneous or mixed sensor elements;
   a first sensor element sequencer and ultrasonic pulser on or connected to the first arm of the forceps;
   a second sensor element sequencer and ultrasonic receiver on or connected to the second arm of the forceps;
   a first controller on or connected to the first arm of the forceps wherein each of the first sensor element sequencer, ultrasonic pulser, and first controller is configured to generate a scan transmission of the transmitting sensor array;
   a second controller on or connected to the second arm of the forceps wherein each of the second sensor element sequencer, ultrasonic receiver and second controller is configured to coordinate with the scan transmission of the transmitting sensor array;
   a data processor;
   a data display device; and
   a three-dimensional motion tracking sensor or position sensor for determining the position of each characteristic measurement during use.

10. The system of claim 9 wherein the two or more homogenous or mixed sensor elements on the receiving array detect a through transmission of at least one of high-frequency ultrasound in the 10-100 MHz range, conductance and dielectric properties in the radiofrequency (RF) range, microwaves, micro-electrical fields, micro-electrical currents, terahertz waves, infrared light, visible light, ultraviolet light, and x-rays.

11. The system of claim 10 wherein the data processor calculates a 2D or 3D image of pathology of a surgical cavity, organ, or other body region where the medical procedure is performed.

12. The system of claim 9 wherein the data processor performs calculations to obtain at least one tissue property that alters the energy that is transmitted through the tissue from the transmitting array and is sensitive to pathology on a microscopic scale, including sound speed, attenuation, microscopic scattering, extinction, fluorescence, absorption, spectral characteristics, and resistivity.

13. The system of claim 12 wherein the data processor interprets at least one calculated tissue property as at least one of a tissue pathology state, a range of states, and a mixture of states.

14. The system of claim 13 wherein the data processor calculates a 2D or 3D microscale image of the pathology of the tissue region between the sensor arrays at the forceps tips using at least one of tomographic reconstruction, charge-coupled device (CCD) array imaging of optical signals, and micro-radiography using a weak radioactive point source and a miniature x-ray area image sensor.

15. The system of claim 9 wherein the data display device comprises at least one of an audio, video, text, and visual display.

16. The system of claim 9 wherein the forceps transmits a tissue/cellular characteristic sensitive signal and receives reflections of the signal from within the tissue.

17. The system of claim 16 wherein the data processor performs calculations based on at least one of ultrasound reflection within tissue, light reflection within tissue, micro-electrical currents within tissue, micro-electric fields within tissue, microwave reflection within tissue, terahertz wave reflection within tissue, tomographic reconstruction of pathology sensitive signals using sensor microarrays, charge-coupled device (CCD) array imaging of optical signals, and phased array imaging of pathology sensitive signals using sensor microarrays.

18. The system of claim 9 further comprising an optical sensor comprised of a monochromatic or polychromatic semiconductor laser array and a monochromatic or polychromatic charge-coupled (CCD) imaging array for through-transmission measurements of at least one of Raman, extinction, fluorescence, and other optical spectra.

19. A method for determining microcellular characteristics of a tissue, the method comprising the steps of:
providing a forceps comprising a first arm comprising at least one transmitting sensor array on a tip of the first arm of the forceps wherein the transmitting sensor array is configured to transmit a microcellular characteristic-sensitive signal through a tissue and wherein the forceps further comprises an opposing second arm comprising a receiving sensor array on the opposing second arm of the forceps wherein the receiving sensor array is configured to receive a microcellular characteristic-sensitive signal through the tissue and wherein each sensor array comprises two or more homogeneous or mixed sensor elements;
applying the transmitting sensor array and the receiving sensor array to an intervening tissue during a surgery or other procedure;
applying a controller module and a sensor element sequencer to modulate a transmitted signal of each sensor element or group of sensor elements in the transmitting sensor array to scan the intervening tissue;
targeting the transmitted signals through the intervening tissue;
applying a second controller module and a second sensor element sequencer to each sensor element or group of sensor elements in the receiving sensor array to coordinate with a scan transmission of the transmitting sensor array;
sending received data to a sensor data receiver module to pre-process data with at least one of an amplifier, filter, and rectifier;
sending pre-processed data to a data processor interpretation module;
applying the data processor interpretation module to construct a 2D or 3D image of a pathology of a surgical cavity, organ, or other body region where a medical or other procedure is performed;
applying the data processor interpretation module to construct a 2D or 3D microscale image of the pathology of a tissue region between the sensor arrays at the forceps tips;
optionally requesting additional data;
observing the interpretation of the data on a data display module; and
adjusting the surgery or other procedure based on the interpreted data.

20. The method of claim 19 wherein the opposing receiving sensor array detects at least one of high-frequency ultrasound in the 10-100 MHz range, conductance and dielectric properties in the radiofrequency (RF) range, microwaves, terahertz waves, infrared light, visible light, ultraviolet light, and x-rays.

21. The method of claim 19 wherein the data processor performs calculations based on at least one of ultrasound transmission through tissue, light transmission through tissue, micro-electrical currents through tissue, micro-electric fields through tissue, microwave transmission through tissue, terahertz wave transmission through tissue, tomographic reconstruction of pathology sensitive signals using sensor microarrays, charge-coupled device (CCD) array imaging of optical signals, micro-radiography using a weak radioactive point source and a miniature x-ray area image sensor.

22. The method of claim 19 wherein the surgery comprises precision cancer surgery.

23. The method of claim 19 wherein the surgery comprises Mohs surgery.

24. The method of claim 19 wherein the transmitting sensor array on the tip of the first arm of the forceps transmits a tissue/cellular characteristic sensitive signal and receives reflections of the signal from within the tissue.

* * * * *